US007427483B2

United States Patent
Nguyen (10) Patent No.: US 7,427,483 B2
(45) Date of Patent: Sep. 23, 2008

(54) **UTILIZATION OF NUCLEOTIDE PROBES IN ELISA PROCEDURE FOR THE QUANTITATIVE DETERMINATION OF *PLASMODIUM FALCIPARUM* DNA IN MALARIA**

(75) Inventor: Khue Vu Nguyen, Carlsbad, CA (US)

(73) Assignee: Vista Biologicals Corporation, Carlsbad, CA (US)

( * ) Notice: Subject to any disclaimer, the term of this patent is extended or adjusted under 35 U.S.C. 154(b) by 346 days.

(21) Appl. No.: 11/307,852

(22) Filed: Feb. 24, 2006

(65) Prior Publication Data

US 2007/0202507 A1    Aug. 30, 2007

(51) Int. Cl.
*C12Q 1/68* (2006.01)
*C12P 19/34* (2006.01)
*G01N 33/00* (2006.01)
*C07H 21/04* (2006.01)

(52) U.S. Cl. .................. 435/6; 435/7.92; 435/91.2; 435/91.52; 536/23.7; 536/24.32; 536/24.33

(58) Field of Classification Search ............... None
See application file for complete search history.

(56) References Cited

U.S. PATENT DOCUMENTS 6,855,316 B1 *   2/2005   Chang et al. ............. 424/185.1

OTHER PUBLICATIONS

Chang, S.P. et al. Experimental Parasitology 67:1-11 (1988).*

* cited by examiner

*Primary Examiner*—Diana B Johannsen (57) ABSTRACT

The present invention is the development of a simple and specific quantitative method for the determination of *P. falciparum* DNA in malaria that involves the direct detection of the highly 42-kDa conserved C-terminal region of *P. falciparum* merozoite surface protein (MSP1) gene. This procedure entails the amplification of the 42-kDa C-terminal region of the MSP1 gene by using the PCR technique in the presence of digoxigenin-11-dUTP and the synthesis of the specific biotin labeled nucleotide probes directed to the 42-kDa C-terminal region of the MSP1 gene. These specific probes are then used in the Enzyme Linked Immunosorbent Assay (ELISA) for the quantitative determination of the 42-kDa C-terminal region of the MSP1 gene which leads to the quantitative determination of *P. falciparum* DNA in malaria for quantitative diagnostic purpose as well as for monitoring the efficacy of antimalarial treatment.

1 Claim, 6 Drawing Sheets

UTILIZATION OF NUCLEOTIDE PROBES IN ELISA PROCEDURE FOR THE QUANTITATIVE DETERMINATION OF PLASMODIUM FALCIPARUM DNA IN MALARIA

The present invention concerns the development of a simple and specific quantitative method for the determination of *Plasmodium falciparum* DNA in malaria that involves the direct detection of the highly 42-kDa conserved C-terminal region of *P. falciparum* merozoite surface protein1 (MSP1) gene. This procedure entails the amplification of the 42-kDa C-terminal region of the MSP1 gene by using the PCR technique in the presence of digoxigenin-11-dUTP and the synthesis of the specific biotin label nucleotide probes directed to the 42-kDa C-terminal region of the MSP1 gene. These specific probes are then used in the Enzyme Linked Immunosorbent Assay (ELISA) for the quantitative determination of the 42-kDa C-terminal region of the MSP1 gene which leads to the quantitative determination of *P. falciparum* DNA in malaria for quantitative diagnostic purpose as well as for monitoring efficacy of antimalarial treatment.

BACKGROUND OF THE INVENTION

Malaria is a tropical disease that is transmitted by *Anopheles* mosquitoes. Forty-one percent of the world's population lives in areas where malaria is transmitted. The global picture of malaria is grim: Worldwide, each year 300 million to 500 million people are infected and more than 1 million die, mostly children under the age of 5 (1). Although the vast majority of these cases are found in the 100 countries in the tropical regions of Africa, Asia, Central and South America where the disease is endemic, the recent increase in population movement to and from endemic areas through tourism and migration due to wars and socioeconomic factors has resulted in higher numbers of imported malaria cases where the disease is not endemic, such as the United States (2) and Europe (3-5). Malaria remains a major global health threat in the $21^{st}$ century. The estimated cost of malaria in terms of strains on the health systems and economic activity lost is enormous. According to UNICEF, malaria costs Africa US$ 12 billions every year in lost productivity, reduced household income and expenditure on treatment. It slows economic growth by 1.3% per year.

Malaria is caused by protozoan parasites belonging to the genus *Plasmodium*. Four species of malaria parasites can infect humans: *Plasmodium falciparum, P. vivax, P. oval* and *P. malariae*. Species differentiation of *Plasmodium* is essential for selecting the proper treatment. Especially important is differentiating *P. falciparum* from the others since this species is responsible for 95% of deaths due to malaria (6). Malaria diagnosis, particularly in remote areas lacking laboratory support, frequently relies on the patient's symptoms. The first symptoms of malaria (fever, chills, sweats, headaches, muscle pains, nausea and vomiting) are not specific to malaria; clinicians often misdiagnose malaria infection. Symptomatic diagnosis is further complicated in highly endemic areas because a large proportion of the population can be infected but are not made ill by these parasites. Malaria morbidity, mortality and transmission can be reduced if infection can be promptly diagnosed and adequately treated.

Concerning the diagnostic procedure, the current standard method for diagnosis of malaria is the microscopic examination of Giemsa-stained thick and thin blood smears (7, 8). This procedure is time-consuming to prepare, read and interpret the slides. Previous studies have shown that even with experienced microscopists, misdiagnosis occurs, particularly in cases of mixed infection or low parasitemia (7, 9). Immunochromatographic assays based on antigen detection have been developed but are also relatively insensitive in cases of low parasitemia (10-12). In addition, antigenemia may persist weeks beyond the actual infection, leading to the false diagnosis of malaria parasitemia (10, 13). Molecular detection for *Plasmodium* diagnosis using the polymerase chain reaction (PCR) has resulted in increased sensitivity and species discrimination compared to either microscopic or immunochromatographic diagnosis of malaria (14, 15, 5, 16). However, most published PCR assays are gel based, resulting in a lengthy procedure not optimal for clinical use. Real-time PCR, a new methodology that employs fluorescent labels to enable the continuous monitoring of amplicon (PCR product) formation throughout the reaction has recently been adapted to detect all four human malaria parasites in blood samples (17-19). However, this procedure is laborious, costly and not suited for any laboratory interested in research related to malaria diagnosis.

Concerning the treatment, a limited number of drugs for treatment of malaria are available today. Due to worsening problems of drug resistance in many parts of the world, adequate treatment of malaria is becoming increasingly difficult. In the Central African Republic, the resistance of *P. falciparum* to chloroquine (CQ), the traditional first-line therapy for uncomplicated *P. falciparum* malaria, has been documented since 1983 (20) and the resistance to sulfadoxine-pyrimethamine (SP) since 1987 (21). The widespread resistance of *P. falciparum* to CQ and SP has also been found in sub-Saharan Africa (22) and on the north coast of Peru (23). Because of growing concerns about the development of resistance to antimalarial drugs when used alone, the affected countries are faced with the challenge of selecting a new first-line regimen and revising antimalarial treatment policies (24). Actually, the combination therapy is increasingly being regarded as the best strategy to improve efficacy and delay the development and spread of drug resistance (25). Evaluations of the efficacy of CQ+SP and amodiaquine (AQ)+SP in Bangui, Central African Republic (22), and SP+artesunate (AS) in Peru (23) for the treatment of uncomplicated *P. falciparum* malaria were performed. The obtained results suggest that the short-term efficacy of AQ+SP regimen is good, its long-term efficacy remains unknown (22). Fever and asexual parasite density decreased significantly and more rapidly in patients treated with SP+AS than in those who received SP alone. No severe adverse drug reactions were observed; however, self-limited rash and pruritis were significantly more common; and an exacerbation of nausea, vomiting, and abdominal pain were observed significantly and more frequently among patients who had received SP-AS combination therapy (23). Although some new drugs have appeared in the last 20 years (e.g., mefloquine, halofantrine, artemisinin derivatives, malarone), new, especially inexpensive and affordable drugs and more practical formulations of existing drugs/compounds are badly needed.

International efforts to combat malaria are also focused on the search for an effective and practical vaccine. There are four general categories of malaria vaccine candidates (26, 27), each representing a different stage of intervention. Virtually all the malaria vaccine candidates (with the exception of anti-disease vaccine described below) are cell surface antigens present during one of the three developmental stages of the *Plasmodium* parasite. 1/ Pre-erythrocytic (sporozoite) vaccines are those directed against the sporozoite (28, 29) and liver stages of the malaria parasite (30, 31). The sporozoite is the form of the parasite introduced into the human host by the bite of an infected mosquito which invades liver cells. A sporozoite vaccine could prevent infection either by blocking invasion of liver cells (antibody response) or destroying infected liver cells (cell-mediated response) by preventing release of parasites into the bloodstream. 2/ The asexual blood-stage (erythrocytic) vaccines (32-36) are directed against the merozoite stage of the parasite, which invades and replicates in the red blood cells. A blood-stage vaccine would be expected to reduce both the severity and duration of the disease by decreasing the blood parasite density, which correlates with reduced disease symptoms and risk of death. 3/ The transmission-blocking vaccines target the sexual stage of the parasite and are designed to raise antibodies (in humans) against the gamete stage of the parasite present in the mosquito gut (37, 38). Such antibodies taken up by a mosquito during a blood meal should block further parasite development in the mosquito, becoming a non-infectious vector. Blocking transmission of the parasite could reduce infectivity of the mosquitoes (carrying fewer parasites) and extend the useful life of a pre-erythrocytic or blood-stage vaccine by preventing transmission of antibody-resistant mutants. 4/ A fourth type of potential malaria vaccine is an anti-disease vaccine (39). This approach to a vaccine involves the identification of parasite toxins that contribute to the disease. An anti-disease vaccine is designed to prevent the anemia, coma, kidney disease and/or fever of malaria. Despite all efforts, none of the work in the above-mentioned four categories of malaria vaccine candidates has resulted in a practical vaccine at the present time.

Taking into account the above-mentioned problems, the present study is focused on *P. falciparum* species because this species is the major pathogen causing lethal malaria (95%) in man (6). The current situation of the clinical development to combat malaria shows that there is a need to design an easy, simple, and cost-effective procedure for the quantitative determination of *P. falciparum* DNA in malaria for quantitative diagnostic purpose and also for monitoring the efficacy of antimalarial treatment. To address such a need, a different approach is used for the development of a quantitative procedure for the determination of *P. falciparum* DNA in malaria. The new approach used in the current invention is different and contrary to previous approaches used for the development of malaria diagnostic tests because it involves the highly 42-kDa conserved C-terminal region of *P. falciparum* merozoite surface protein1 (MSP1) gene, in order to minimize all problems related to misdiagnosis of malaria, and because it involves the use of specific biotin label nucleotide probes directed to the 42-kDa C-terminal region of the MSP1 gene. Indeed, it is well known that the MSP1 is part of a complex that is thought to be involved in red blood cell invasion (40-43). Any research work for the development of a molecular diagnostic test, antimalarial drug or malaria vaccine that is based on the highly 42-kDa conserved C-terminal region of the MSP1 gene would consequently be useful to overcome all problems of misdiagnosis, drug resistance due to mutations in *P. falciparum* DNA. This new procedure entails the amplification of the 42-kDa C-terminal region of the MSP1 gene by using the PCR technique in the presence of digoxigenin-11-dUTP and the synthesis of the specific biotin label nucleotide probes directed to the 42-kDa C-terminal region of the MSP1 gene. These specific probes are then used in the Enzyme Linked Immunosorbent Assay (ELISA) for the quantitative determination of the 42-kDa C-terminal region of the MSP1 gene which leads to the quantitative determination of *P. falciparum* DNA in malaria for quantitative diagnostic purpose.

The use of the specific probes allows the development of an easy and simple procedure for quantitative molecular diagnostic testing.

PURPOSE OF THE INVENTION

The purpose of the invention is to develop an easy, simple and cost-effective procedure for the quantitative determination of *Plasmodium falciparum* DNA in malaria for quantitative diagnostic purpose. The procedure is based on the presence of the highly 42-kDa conserved C-terminal region of *Plasmodium falciparum* merozoite surface protein1 (MSP1) gene. The method of the present invention entails the following procedure: 1/ Amplifying the 42-kDa C-terminal region of the MSP1 gene by using the PCR technique in the presence of digoxigenin-11-dUTP from the negative control (non-infected) and infected samples; 2/ Performing the synthesis of the specific biotin label nucleotide probes directed to the 42-kDa C-terminal region of the MSP1 gene; 3/ Performing the ELISA procedure using the immobilized streptavidin on polystyrene microtitration plates for the quantitative determination of the 42-kDa C-terminal region of the MSP1 gene which leads to the quantitative determination *P. falciparum* DNA in malaria for quantitative diagnostic purpose. Furthermore, this quantitative ELISA method could also be useful for monitoring the efficacy of antimalarial treatment as well as for evaluating efficacy of the MSP1 which is currently used as a major candidate for a blood-stage malaria vaccine antigen.

BRIEF DESCRIPTION OF THE DRAWINGS

M: Marker (kb)

Lane 1: Negative control (absence of *P. falciparum* DNA)—absence of digoxigenin-11-dUTP Lane 2: Presence of *P. falciparum* DNA—absence of digoxigenin-11-dUTP Lane 3: Presence of *P. falciparum* DNA—absence of digoxigenin-11-dUTP Lane 4: Negative control (absence of *P. falciparum* DNA)—presence of digoxigenin-11-dUTP Lane 5: Presence of *P. falciparum* DNA—presence of digoxigenin-11-dUTP Lane 6: Presence of *P. falciparum* DNA—presence of digoxigenin-11-dUTP

M: Marker (kb)

Lane 1: Fragment 1 (420 bp)

Lane 2: Fragment 2 (420 bp)

Lane 3: Fragment 3 (379 bp)

M: Marker (kb)

Lanes 1 to 6: Presence of *P. falciparum* DNA (µg/mL) at the concentration of 550, 275, 137.50, 68.75, 34.375, and 17.185 µg/mL for the lanes 1 to 6 respectively.

MATERIALS AND METHODS

Isolation of *Plasmodium falciparum* DNA

*P. falciparum* was cultured by the method of Trager and Jensen (44). Genomic DNA was extracted from in vitro-cultured parasites by standard methods (45). The isolated DNA was then dissolved in water pretreated by 0.1% diethyl pyrocarbonate (DEPC, Sigma, St. Louis, Mo., U.S.A.). This DNA solution was used as a template for the amplification of the 42-kDa C-terminal region of the MSP1 gene.

Amplification

Amplification in the absence of digoxigenin-11-dUTP

The amplification of the 42-kDa C-terminal region of the MSP1 gene was assessed by the PCR technique (46, 47). Two synthesized oligonucleotides, forward primer (SEQ ID NO. 1) and reverse primer (SEQ ID NO. 2) (Invitrogen, Carlsbad, Calif., U.S.A.) were used. They have the following sequences:

```
5' ATTGGATCCACTAAAATGTGGTCTTGGAAGTGTCTTTTATTCTGGGCTGT 3'    (SEQ ID NO. 1)
(forward primer) and 5' CGTAGGTACCTTATTAAGGTGGGGAGCAGAAGATACC 3'    (SEQ ID NO. 2)
(reverse primer)
```

The oligonucleotide (SEQ ID NO. 1) (forward primer) was based on the sequence between base pairs 1 to 50 of the C-terminal region of the MSP1 gene of the Uganda-Palo Alto *P. falciparum* isolate (FUP) (44). The oligonucleotide (SEQ ID NO. 2) (reverse primer) was selected by taking the complementary sequence between base pairs 1183 and 1219 of the C-terminal region of the MSP1 gene of the Uganda-Palo Alto *P. falciparum* isolate (FUP) (48). Amplification was conducted by using a DNA Thermal Cycler (Amplitron®II Thermolyne). The reaction was conducted in a total volume of 50 μL with 2.5 units of Taq DNA polymerase (Invitrogen, Carlsbad, Calif., U.S.A.) in the presence of the PCR reaction buffer from Invitrogen kit containing $2\times10^3$ nM each of oligonucleotides, 200 μL each of nucleotides dATP, dCTP, dGTP, and dTTP, $12.5\times10^2$ nM of MgCl$_2$ and 1 μL of the solution of *P. falciparum* DNA obtained previously (positive sample). For the negative control (absence of *P. falciparum* DNA), 1 μL of distilled water was used. Amplification conditions were as follow: Denaturing at 94° C. for 1 min, annealing at 55° C. for 2 min, and elongation at 72° C. for 1 min each, unless otherwise noted, for 35 cycles. The PCR products were analyzed by electrophoresis on a 20 g/L agarose gel to screen for the presence of appropriate-size band using the fluorescent dye ethidium bromide.

Amplification in the Presence of Digoxigenin-11-dUTP

Amplifying the 42-kDa C-terminal region of the MSP1 gene by the PCR technique (46, 47) was also performed in the presence of 10 μM of digoxigenin-11-dUTP (Roche), 190 μM each of nucleotides dATP, dCTP, dGTP. The same amplification conditions for PCR as mentioned-above were used. The PCR products were analyzed by electrophoresis on a 20 g/L agarose gel to screen for the presence of the appropriate-size band using the fluorescent dye ethidium bromide. The labeling of nucleic acids with digoxigenin was visualized by the transfer of the DNA fragments to 40 cm$^2$ of the nitrocellulose membrane according to the transfer technique described by Southern (49). The nitrocellulose membrane was then blocked in 12 mL/cm$^2$ of blocking solution—2% bovine serum albumin (BSA) in phosphate-buffered saline (PBS). After incubation for 1 h at 37° C., the nitrocellulose membrane was washed with PBS and then incubated for 1 h at 37° C. in 12 mL/cm$^2$ of blocking solution containing 0.1% Tween®20 and 3 μL of anti-digoxigenin antibody from sheep, conjugated with alkaline phosphatase (Boehringer Mannheim, BmbH, Germany). Then, the nitrocellulose membrane was washed with PBS and alkaline phosphatase activity was measured in the presence of chemiluminescent substrate (CDP-Star™; Boehringer Mannheim, GmbH, Germany). After incubation for 5 min at room temperature, autoradiography was developed using the BIOMAX™MR emulsion film (Eastman Kodak Co., Rochester, N.Y. 14650, U.S.A.).

Construction of the Biotin Labeled Nucleotide Probes

Amplification

The synthesis of three specific biotin label nucleotide probes 7, 8, and 9 directed to the 42-kDa C-terminal region of the MSP1 gene was performed. The 42-kDa C-terminal region of the MSP1 gene was first used as template for the amplification of the three DNA fragments 1, 2, and 3 of the 42-kDa C-terminal region of the MSP1 gene using the synthesized oligonucleotides (SEQ ID NO. 1) and (SEQ ID NO. 3) for the fragment 1, (SEQ ID NO. 4) and (SEQ ID NO. 5) for the fragment 2, (SEQ ID NO. 6) and (SEQ ID NO. 2) for the fragment 3. The sequences of the oligonucleotides (SEQ ID NO. 3), (SEQ ID NO. 4), (SEQ ID NO. 5), and (SEQ ID NO. 6) are:

```
5' GAACTTGATGTCGTTCTCAAC 3'    (SEQ ID NO. 3)    (reverse primer)

5' GTTGAGAACGACATCAAGTTC 3'    (SEQ ID NO. 4)    (forward primer)
```

```
5' CAGTTTTCCAAGCATGTCTTTC 3'    (SEQ ID NO. 5)   (reverse primer)

5' GAAAGACATGCTTGGAAAACTG 3'    (SEQ ID NO. 6)   (forward primer)
```

The oligonucleotides (SEQ ID NO. 3) and (SEQ ID NO. 5) (reverse primers) were based on the sequences between base pairs 400 to 420 and 819 to 840, respectively, of the C-terminal region of the MSP1 gene of the Uganda-Palo Alto *P. falciparum* isolate (FUP) (48), in this case, however, taking the complementary sequence to allow PCR. The oligonucleotides (SEQ ID NO. 4) and (SEQ ID NO. 6) (forward primers) were based on the sequences between base pairs 400 to 420 and 819 to 840, respectively, of the C-terminal region of the MSP1 gene of the Uganda-Palo Alto *P. falciparum* isolate (FUP) (48). The PCR reaction was conducted in a total volume of 50 μL with 2.5 units of Taq DNA polymerase (Invitrogen, Carlsbad, Calif., U.S.A.) in the presence of the PCR reaction buffer from Invitrogen kit containing $2 \times 10^3$ nM each of oligonucleotides, 200 μM each of nucleotides dATP, dCTP, dGTP, and dTTP, $12.5 \times 10^2$ nM of $MgCL_2$ and 1 μL of the solution of *P. falciparum* DNA obtained previously. Amplification conditions were as follow: Denaturating at 94° C. for 1 min, annealing at 65° C. for 2 min, and elongation at 72° C. for 1 min each for 35 cycles. The PCR products obtained were the DNA fragments 1, 2, and 3 which were analyzed by electrophoresis on a 20 g/L agarose gel to screen for the presence of the appropriate-size band using the fluorescent dye ethidium bromide. The DNA fragments 1, 2, and 3 were then isolated by phenol-chloroform extraction, dried and resuspended in distilled water according to the method described by Sambrook et al. (50).

Cloning

The obtained purified DNA fragments 1, 2, and 3 were then subjected to the ligation reaction in the pCR® 2.1 plasmid vector of the TA Cloning kit (Invitrogen, Carlsbad, Calif., U.S.A.). The reagents of this kit and the reaction conditions used were according to the manufacturer's recommendations. The ligation product was then introduced in TOP1OF' *E. Coli* strain by using the reagents and the transformation procedure of the TA Cloning kit (Invitrogen, Carlsbad, Calif., U.S.A.). The screening for inserts was performed by using blue-white color selection. The sequencing of obtained inserts was performed by using the ABI DNA sequencer. The resulting vectors (pCR® 2.1/$DNA_{1,2,3}$) were termed 4, 5, and 6 for the pCR® 2.1/$DNA_1$, pCR® 2.1/$DNA_2$, and pCR® 2.1/$DNA_3$ respectively.

Synthesis of the Biotin Label Probes

From the previously obtained vectors 4, 5, and 6, the SpeI-XhoI fragments, containing the DNA fragments 1, 2, and 3 respectively, were isolated and used as templates for the synthesis of three specific biotin label nucleotide probes 7, 8, and 9 respectively. The reaction was conducted in the presence of the reagents for the preparation of biotinylated probes (BioPrimeR DNA Labeling System, Invitrogen, Carlsbad, Calif., U.S.A.). The primers (SEQ ID NO. 1) and (SEQ ID NO. 3), (SEQ ID NO. 4) and (SEQ ID NO. 5), (SEQ ID NO. 6) and (SEQ ID NO. 2) were used for the synthesis of the specific probes 7, 8, and 9 respectively. The reaction conditions used were according to the manufacturer's recommendations. The labeling of nucleotide probes with biotin was visualized using the same conditions as that used for visualization of digoxigenin-labeled nucleic acids. In this case, 15 μL of anti-biotin-monoclonal antibody conjugated with alkaline phosphatase (Boehringer Mannheim, GmbH, Germany) in 12 $mL/cm^2$ of bloking solution containing 0.1% (V/V) Tween®20 were used.

Use of Biotin Labeled Nucleotide Probes in ELISA Procedure

Immobilized streptavidin on polystyrene microtitration plates (SigmaScreen™, Streptavidin coated plate) (Sigma, St. Louis, Mo., U.S.A.) were used for the assays. All washes were performed four times with PBS containing 0.05% (V/V) Tween®20 (PBS-T). The substrate solution for alkaline phosphatase (p-nitrophenyl phosphate, pNPP, 1 g/L in 0.2M Tris-HCl buffer, pH 7) was from Sigma, St. Louis, Mo., U.S.A. After incubation for 30 min at 37° C., the reaction was stopped by the addition of 3M NaOH (50 μL per well). The optical density at 405 nm ($O.D._{\lambda=405\ nm}$) was measured in a microplate colorimeter (Molecular Devices, Thermomax Microplate Reader).

For the assays, the *P. falciparum* DNA, isolated from negative control and from positive samples using the standard methods (45), was first subjected to PCR in the presence or absence of digoxigenin-11-dUTP as described above. An aliquot of 5 μL of each PCR product was removed and added to a mixture composed of 15 μL of hybridization solution (4× standard saline citrate, SSC, 40% formamide, 40× Denhardt), 6 μL of salmon sperm DNA (1 mg/mL), 5 μL of biotin-labeled nucleotide probes 7, 8, and 9 and 29 μL of distilled water. After denaturation at 97° C. for 10 min, hybridization was performed for 1 h at 42° C. After hybridization, 55 μL of the reaction medium was removed and added to the immobilized streptavidin plates. After incubation for 1 h at 37° C., the plates were washed, and 100 μL of a 1 in 1,000 dilution of alkaline phosphatase antibody anti-digoxigenin, Fab fragments (Roche) in PBS-T containing 2% BSA (PBS-T-BSA) was added. After being incubated again for 1 h at 37° C., the plates were washed, and the substrate solution for alkaline phosphatase was added.

RESULTS AND DISCUSSION

Amplification of the 42-kDa C-terminal region of the MSP1 gene

Figure 1:
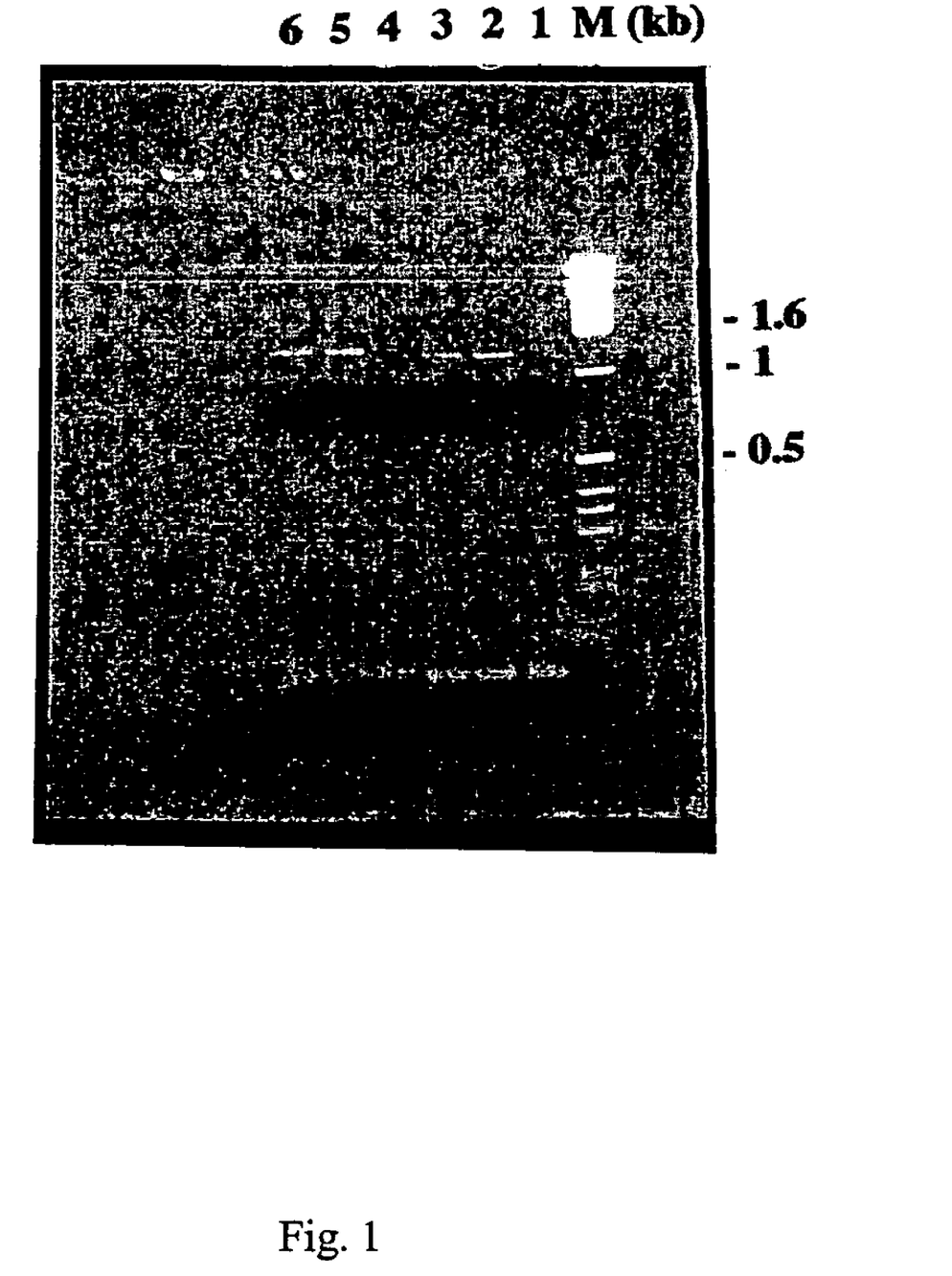
FIG. 1: PCR amplification of the 42-kDa C-terminal region of the MSP1 gene in the presence or absence of digoxigenin-11-dUTP.

The results of the study show that the PCR product of the 42-kDa C-terminal region of the MSP1 gene (1,116 bp) was successfully amplified in the presence or absence of digoxigenin-11-dUTP by using two synthesized oligonucleotides (SEQ ID NO. 1) and (SEQ ID NO. 2) (FIG. 1). The analysis of the PCR product of the 42-kDa C-terminal region of the MSP1 gene completely matched with the sequences of the C-terminal region of the MSP1 gene of the Uganda-Palo Alto *P. falciparum* isolate (FUP) (48).

Synthesis of Biotin Label Probes

Figure 2:
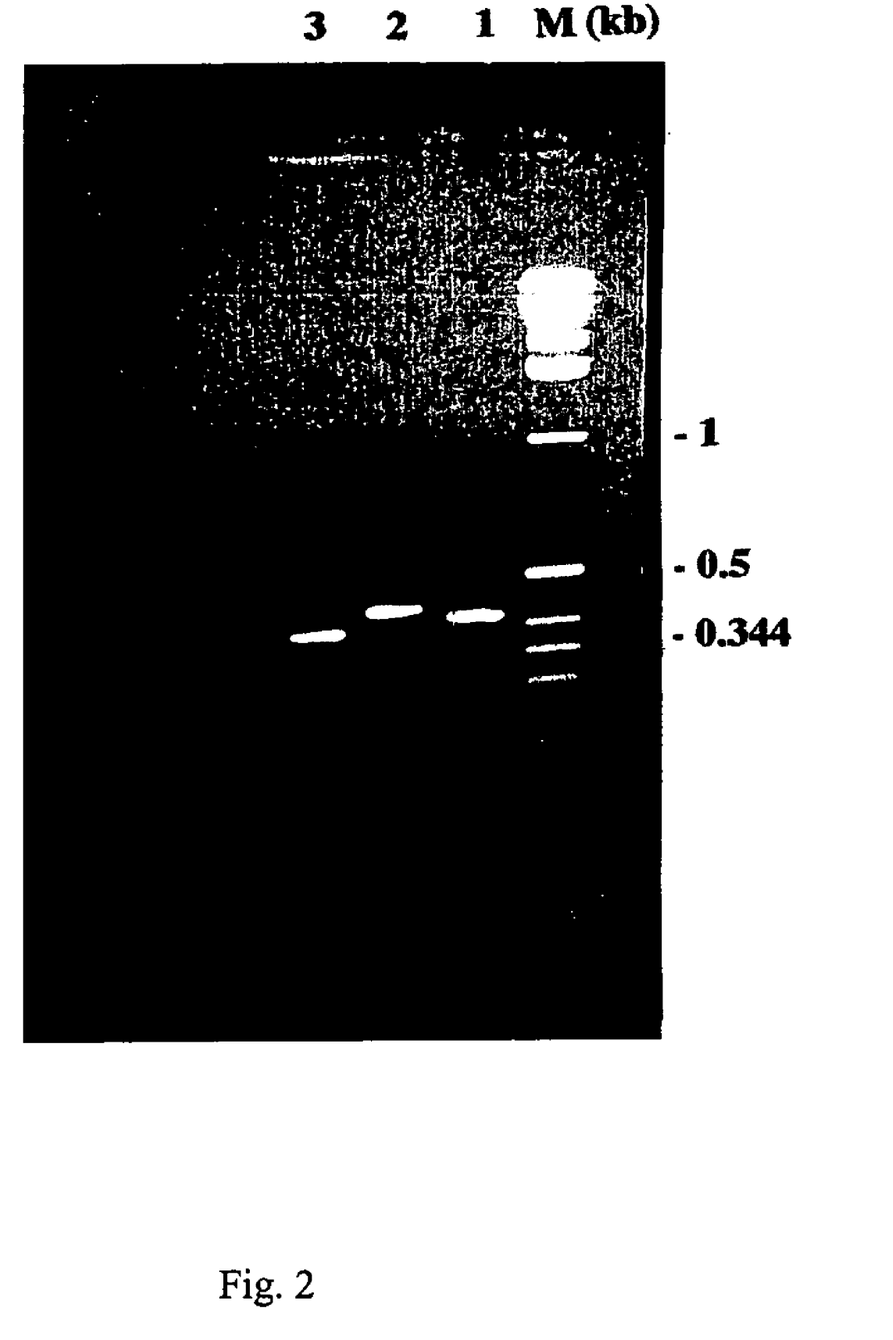
FIG. 2: PCR amplification of the DNA fragments located in the coding region of the 42-kDa C-terminal of the MSP1 gene.

As shown in FIG. 2, the PCR products of the DNA fragments 1, 2, and 3 of 420 bp, 420 bp, and 379 bp respectively were successfully amplified by using the synthesized oligonucleotides (SEQ ID NO. 1) and (SEQ ID NO. 3), (SEQ ID NO. 4) and (SEQ ID NO. 5), (SEQ ID NO. 6) and (SEQ ID NO. 2) for the DNA fragments 1, 2, and 3 respectively. These DNA fragments 1, 2, and 3 were subcloned into the pCR®2.1 plasmid vector of 3.9 kb. The analysis of the sequence of inserts showed that the DNA sequence of these DNA fragments 1, 2, and 3 completely matched with the sequences of the 42-kDa C-terminal gene of the MSP1 gene of the Uganda-Palo Alto *P. falciparum* isolate (FUP) (48). The isolated SpeI-XhoI fragments containing the DNA fragments 1, 2, and 3 were used as templates for the synthesis of three specific biotin label nucleotide probes 7, 8, and 9 respectively. All of these three probes 7, 8, and 9 are directed to the 42-kDa C-terminal region of the MSP1 gene. The efficiency of these probes 7, 8, and 9 (0.56 ng each) was found in the ELISA procedure for the detection of the 42-kDa C-terminal region of the MSP1 gene from the PCR products obtained for 35 cycles of amplification of the 42-kDa MSP1 C-terminal region of the MSP1 gene in the presence or absence of digoxigenin-11-dUTP (FIG. 1). In the absence of digoxigenin-11-dUTP, the results showed that the $O.D._{\lambda=405\ nm}$ obtained with the PCR products for amplification of the 42-kDa C-terminal region of the MSP1 gene were 0.131, 0.127, 0.133; 0.123 0.128, 0.140; 0.117, 0.124, 0.147 for the probes 7, 8, and 9 respectively (Table 1). These $O.D._{\lambda=405\ nm}$ values correspond to the backgrounds. The mean background values corresponding were then 0.130, 0.130, and 0.129 for the probes 7, 8, and 9 respectively. In this study, an $O.D._{\lambda=405\ nm}$ value higher than twice the mean background value was considered as a suitable cutoff i.e. 0.260, 0.260, and 0.258 for the probes 7, 8, and 9 respectively. Therefore, all samples yielding an $O.D._{\lambda=405\ nm}$ value greater than 0.260, 0.260, and 0.258 for the probes 7, 8, and 9 respectively were considered positive for infection, whereas those with an $O.D._{\lambda=405\ nm}$ value less than these cutoff values were scored as negative; also, because the $O.D._{\lambda=405\ nm}$ values obtained from the substrate solution for alkaline phosphatase (0.127, 0.138, 0.126) are similar to those of the backgrounds (Table 1), the $O.D._{\lambda=405\ nm}$ values obtained for the substrate solution for alkaline phosphatase can be used for the determination of the cutoff value. In this case, the mean background value is 0.130 and the cutoff is 0.260. In the presence of digoxigenin-11-dUTP, there was a perfect concordance of the results obtained between the ELISA procedure and the electrophoresis analysis of the PCR products on the 20 g/L agarose gel regarding the negative control and positive sample (FIG. 1 and Table 1). All $O.D._{\lambda=405\ nm}$ values obtained for the negative control were significantly less than the cutoff values (0.209, 0.163, and 0.132 for the probes 7, 8, and 9 respectively). Concerning the positive samples, all $O.D._{\lambda=405\ nm}$ values obtained were much greater than the cutoff values (1.584, 1.328; 1.695, 1.421; 0.737, 0.721 for the probes 7, 8, and 9 respectively (Table 1). The difference in the amount of the PCR product (i.e. the 42-kDa C-terminal region of the MSP1 gene), qualitatively detected by agarose gel electrophoresis (FIG. 1), was also quantitatively detected by ELISA method (1.584 and 1.328 i.e. 19.27% of difference detected using the probe 7; 1.695 and 1.421 i.e. 19.28% of difference detected using the probe 8; 0.737 and 0.721 i.e. 2.21% of difference detected using the probe 9 respectively) (Table 1). Therefore, the probes 7 and 8 directed to the 42-kDa C-terminal region of the MSP1 gene are very effective for the detection of the presence of the 42-kDa C-terminal region of the MSP1 gene. The probe 9 appears less effective. In any case, the difference in accessibility to the different specific regions of the 42-kDa C-terminal region of the MSP1 gene by the probes 7, 8, and 9 is one of the main factor responsible for the difference in efficiency of the probes 7, 8, and 9 for the detection of the presence of the 42-kDa C-terminal region of the MSP1 gene.

Quantitative Determination of the 42-kDa C-Terminal Region of the MSP1 Gene

Figure 3:
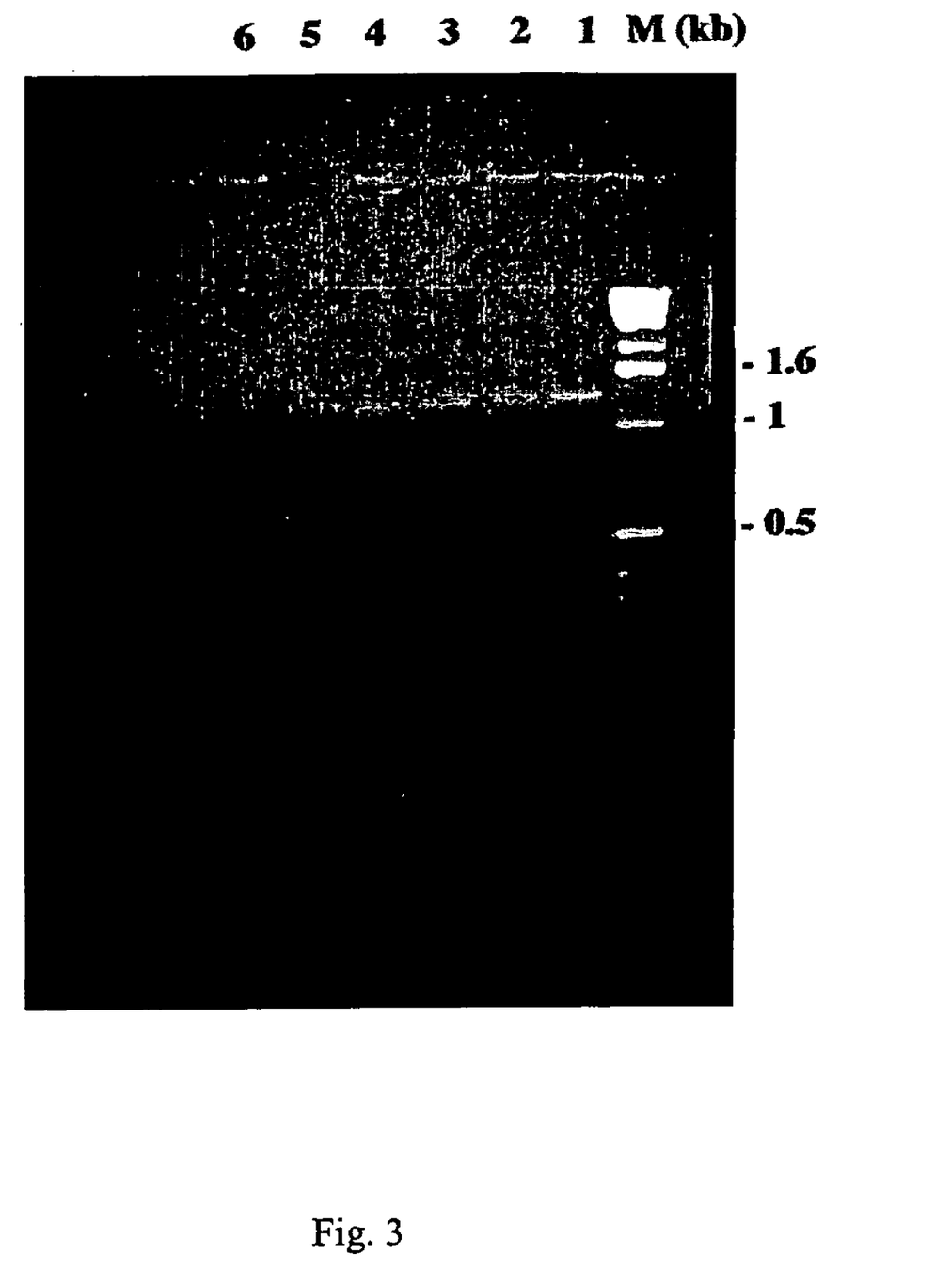
FIG. 3: Quantitative PCR amplification for 20 cycles of the 42-kDa C-terminal region of the MSP1 gene in the presence of digoxigenin-11-dUTP.
Figure 4:
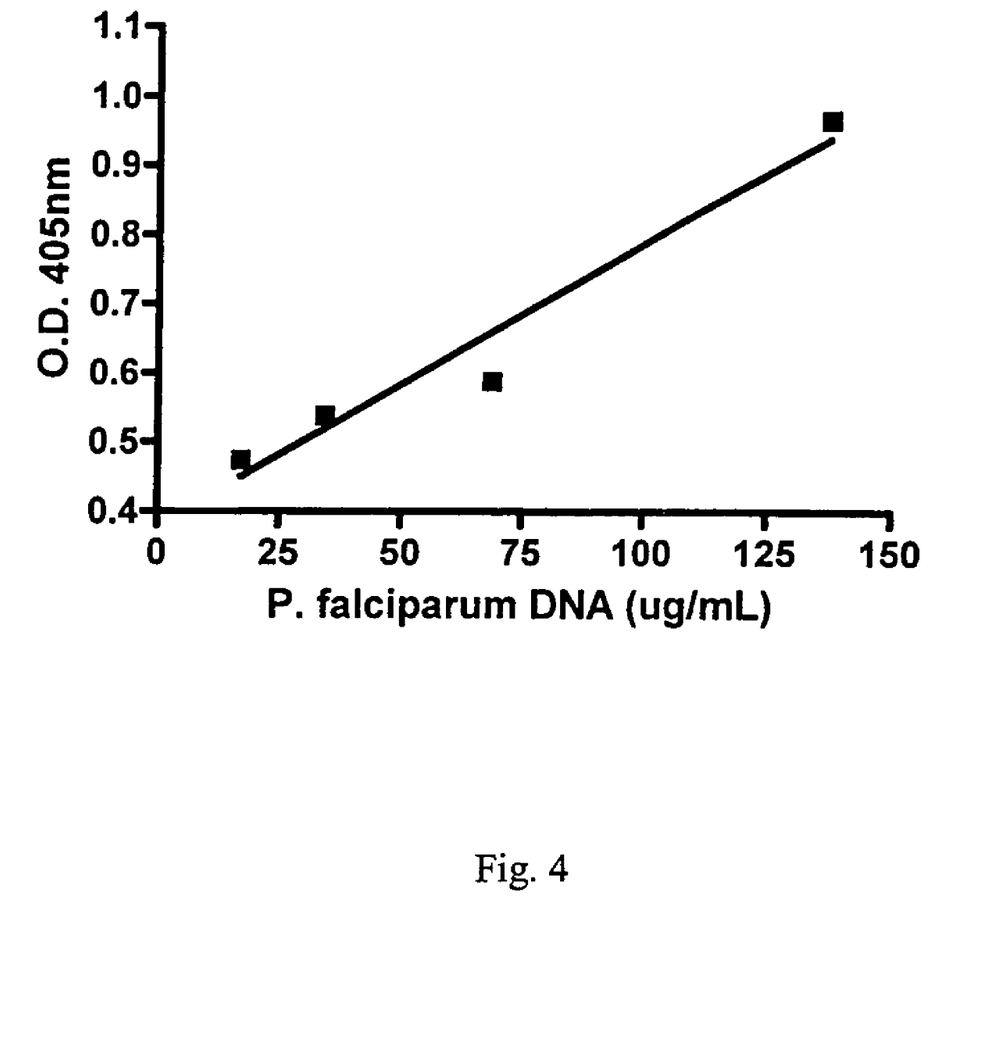
FIG. 4: Standard curve for the quantitative determination of the 42-kDa C-terminal region of the MSP1 gene by using the biotin label probe 8 alone (0.56 ng). Each point represents the average value from the duplicate samples with a relative mean deviation lower than 1%. The line is drawn by linear regression where y is the O.D.$_{\lambda=405\,nm}$ and x the concentration of the *P. falciparum* DNA (μg/mL) (y=0.004080x+0.3790, $r^2$=0.9537).
Figure 5:
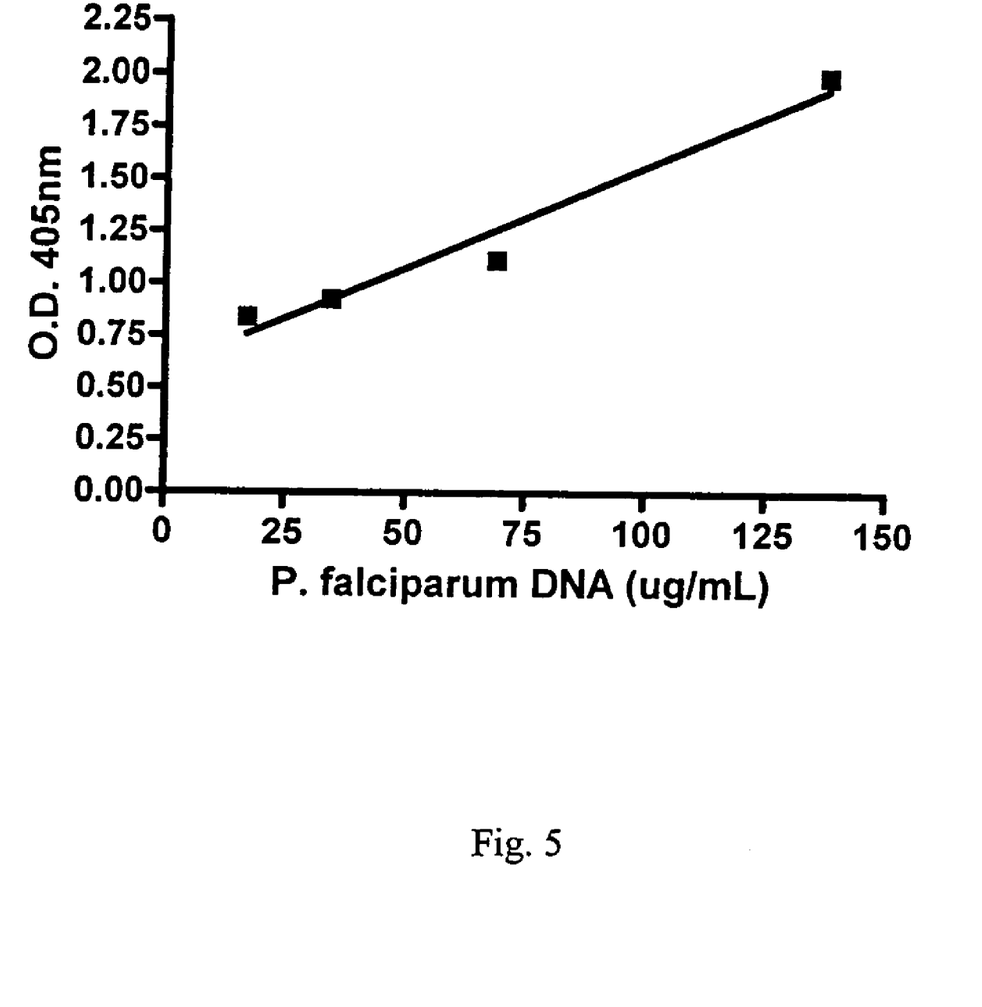
FIG. 5: Standard curve for the quantitative determination of the 42-kDa C-terminal region of the MSP1 gene by using the biotin label probe 8 alone (1.4 ng). Each point represents the average value from the duplicate samples with a relative mean deviation lower than 1%. The line is drawn by linear regression where y is the O.D.$_{\lambda=405\,nm}$ and x the concentration of the *P. falciparum* DNA (μg/mL) (y=0.009760x+0.5887, $r^2$=0.9620).
Figure 6:
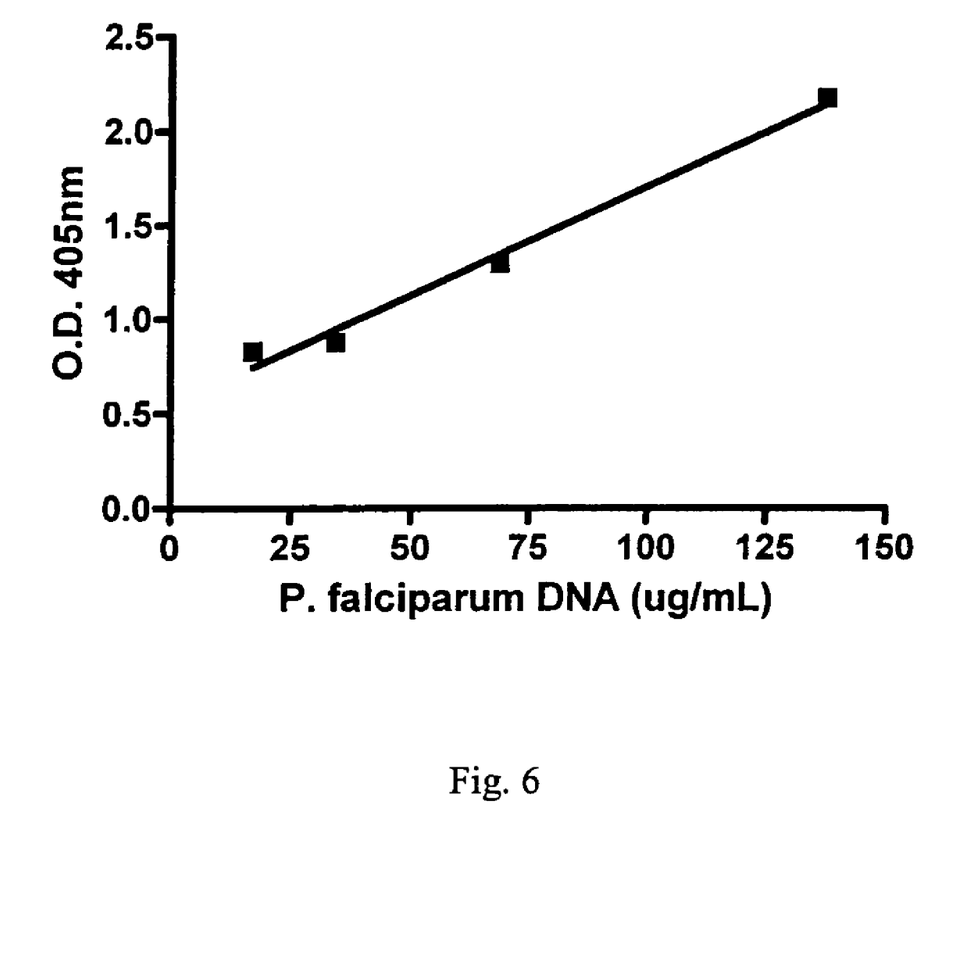
FIG. 6: Standard curve for the quantitative determination of the 42-kDa C-terminal region of the MSP1 gene by combination use of the biotin label probes 7, 8, and 9 (0,56 ng each). Each point represents the average value from the duplicate samples with a relative mean deviation lower than 1%. The line is drawn by linear regression where y is the O.D.$_{\lambda=405\,nm}$ and x the concentration of the *P. falciparum* DNA (μg/mL) (y=0.01166x+0.5440, $r^2$=0.9870).

For the quantitative determination of the 42-kDa C-terminal region of the MSP1 gene, the 20 cycles of the PCR reaction was selected to ensure quantitative measurements during the linear phase (51). Then, the different dilutions of the known original concentration of the *P. falciparum* DNA stock (550 µg/mL) were subjected to the PCR reaction in the presence of digoxigenin-11-dUTP and for 20 cycles. The qualitative results of agarose gel electrophoresis of the PCR product (i.e. the 42-kDa C-terminal region of the MSP1 gene) provided in FIG. 3 show that a quantitative measurement of the 42-kDa C-terminal region of the MSP1 gene can be performed with the PCR reaction for 20 cycles. Indeed, the results show a decrease of the intensity of the appropriate-size band of the PCR product (1,116 bp) with the increase of dilutions from 137.50 µg/mL to 17.18 µg/mL of the *P. falciparum* DNA stock (550 µg/mL). There was no significant difference in intensity of the appropriate-size band of the PCR product for the dilutions greater than 137.50 µg/mL of the *P. falciparum* DNA stock. The results of quantitative determination of the 42-kDa C-terminal region of the MSP1 gene by ELISA technique using the specific probe 8 alone (0.56 ng or 1.4 ng) as well as the results obtained from the cooperative effect in the combination use of the specific probes 7, 8, and 9 (0.56 ng each) are presented in Table 2; here, the cutoff value of 0.260 based on the $O.D._{\lambda=405\ nm}$ values of the substrate solution for alkaline phosphatase (Table 1) was used for the consideration of the presence or absence of the 42-kDa C-terminal region of the MSP1 gene. There was a perfect concordance between the results obtained from the quantitative ELISA procedure and the qualitative results from the agarose gel electrophoresis of the PCR product for the probe 8 alone (0.56 ng or 1.4 ng) and for the combination use of the probes 7, 8, and 9 (0.56 ng each) (Table 2 and FIG. 3). The ELISA results obtained by using the specific probe 8 alone (0.56 ng or 1.4 ng) as well as the results obtained from the cooperative effect in combination use of the specific probes 7, 8, and 9 (0.56 ng each) (Table 2) were exploited: The plot of the $O.D._{\lambda=405\ nm}$ against the concentration of *P. falciparum* DNA (µg/mL) generated a straight line in each case, specific probe 8 alone (0.56 ng) in FIG. 4, (1.4 ng) in FIG. 5, and the combination use of the probes 7, 8, and 9 (0.56 ng each) in FIG. 6. The results for all cases thus show that the linear range for quantitative determination of the 42-kDa C-terminal region of the MSP1 gene was between 17.18 µg/mL and 137.50 µg/mL of *P. falciparum* DNA. The linear regression equations where y is the $O.D._{\lambda=405\ nm}$ and x the concentration of *P. falciparum* DNA (µg/mL): y=0.004080x+0.3790, $r^2$=0.9537, and y=0.009760x+0.5887, $r^2$=0.9620 are for the use of the probe 8 alone with 0.56 ng (FIG. 4) or 1.4 ng (FIG. 5) respectively, and y=0.01166x+0.5440, $r^2$=0.9870 is for the combination use of the probes 7, 8, and 9 (0.56 ng each) (FIG. 6). Furthermore, as the cutoff value was 0.260, the detection limit of this method would be much lower than 17.18 µg/mL. Indeed, by using the probe 8 alone (0.56 ng or 1.4 ng) or by combination use of the probes 7, 8, and 9 (0.56 ng each), the $O.D._{\lambda=405\ nm}$ values obtained for 17.18 µg/mL were much higher than 0.260; they were 0.474 (probe 8, 0.56 ng), 0.839 (probe 8, 1.4 ng), and 0.830 (combination use of the probes 7, 8, and 9, 0.56 ng each) respectively (Table 2). Moreover, the sensitivity of this method would be much better by performing the quantitative determination of the 42-kDa C-terminal region of the MSP1 gene using more amount of the probes 8 or using more amount of the probes 7, 8, and 9 in the combination use of these three probes.

The results show that using the specific biotin label nucleotide probes directed to the highly 42-kDa conserved C-terminal region of the MSP1 gene of *P. falciparum* allows the development of an easy, simple, and cost-effective procedure for the quantitative determination of *P. falciparum* DNA in malaria for diagnostic purpose and for monitoring the efficacy of antimalarial treatment. In this study, the reason for the selection of the highly 42-kDa conserved C-terminal region of MSP1 gene is based on an array of evidence obtained through different studies, which suggest the potential of the highly 42-kDa conserved C-terminal region of MSP1 gene of *P. falciparum* in the development of *P. falciparum* malaria diagnostic, monitoring test, antimalarial drug as well as malaria vaccine. Each species of malaria parasite has a single MSP1 gene that expresses a 185-250 kDa protein attached to the plasma membrane of intraerythrocytic schizonts (52). MSP1 forms part of a complex that is thought to be involved in red blood-cell invasion and antibodies to MSP1 have been shown to block parasite invasion of red blood cells in-vitro (40-43). Several research studies have shown that non-human primates can be protected against *P. falciparum* infection by vaccination with MSP1 isolated from culture parasites (53-55). Studies performed with the analogous MSP1 protein of rodent malaria parasites have indicated that the highly conserved C-terminal region of this molecule contains epitopes critical for the generation of a protective immune response (56, 57). Preservation of disulfide-dependent conformational determinants of the C-terminal region of MSP1 is critical for optimal antigenicity and immunogenicity of the recombinant polypeptide. Chang et al. have developed a C-terminal 42-kDa P. falciparum MSP1 construct in a baculovirus expression system capable of inducing antibodies that inhibit in-vitro *P. falciparum* growth (58) and protect Aotus monkeys against *P. falciparum* malaria (59). Therefore, the highly 42-kDa conserved C-terminal region of MSP1 gene appears to be an effective target for the quantitative determination of *P. falciparum* DNA in malaria for quantitative diagnostic purpose and for monitoring the efficacy of antimalarial treatment. Furthermore, the 42-kDa C-terminal moiety could be used as candidate for the development of a new, inexpensive and affordable antimalarial drug as well as candidate for a blood-stage malaria vaccine antigen.

CONCLUSION

The reported study offers a new approach to the diagnosis of *P. falciparum* malaria which involves the direct detection of the highly 42-kDa conserved C-terminal region of *P. falciparum* merozoite surface protein1 (MSP1) gene, and the use of specific probes in ELISA procedure for the quantitative determination of the 42-kDa region of the MSP1 gene which leads to the quantitative determination of *P. falciparum* DNA in malaria for quantitative diagnostic purpose. The procedure entails the amplification of the 42-kDa C-terminal region of the MSP1 gene by using the PCR technique in the presence of digoxigenin-11-dUTP and the synthesis of the specific biotin label nucleotide probes directed to the 42-kDa C-terminal region of the MSP1 gene. Furthermore, this quantitative ELISA method is also useful for monitoring efficacy of antimalarial treatment as well as for evaluating the efficacy of the MSP1 which is currently used as major candidate for a blood-stage malaria vaccine antigen. This new invention is thus useful for further research work based on the 42-kDa C-terminal moiety of the MSP1 for the development of antimalarial drug as well as malaria vaccine.

REFERENCES

1. World Health Organization. 1999. Malaria, 1982-1997. Weekly Epidemiological Record 74: 265-272.
2. Palmer, C J., J. Alfreds Bonilla, D. A. Bruckner, E. D. Barnett, N. S. Miller, M. A. Haseeb, J. R. Masci, and W. M. Stauffer. 2003. Multicenter study to evaluate the OptiMal test for rapid diagnosis of malaria in U.S. hospitals. J. Clin. Microbiol. 41: 51 78-5182.
3. Romi, R., D. Boccolini, and G. Majori. 1999. Malaria surveillance in Italy: 1997 analysis and 1998 provisional data. Eurosurveillance 4: 85-87.
4. Rubio, J. M., A. Benito, P J. Berzosa, J. Roche, M. Puente, M. Subirats, R. Lopez-Velez, M. L. Garcia, and J. Alvar. 1999. Usefulness of seminested multiplex PCR in surveillance of imported malaria in Spain. J. Cli. Microbiol. 37: 3260-3264.
5. Myjak, P., W. Nahorski, N. J. Pieniazek, and H. Pietkiewicz. 2002. Usefulness of PCR for diagnosis of imported malaria in Poland. Eur. J. Clin. Microbiol. Infect. Dis. 21: 215-218.
6. Stoppacher, R., and S. P. Adams. 2003. Malaria deaths in the United States: Case report and review of deaths, 1979-1998. J. Forensic Sci. 48: 404-408.
7. Payne, D. 1988. Use and limitation of light microscopy for diagnosing malaria at the primary health care level. Bull. W. H. O. 66: 621-626.
8. Warhurst, D. C., and J. E. Williams. 1996. Laboratory diagnosis of malaria: ACO broadsheet no. 148. J. Clin. Pathol. 49: 533-538.
9. Hanscheid, T. 2003. Current strategies to avoid misdiagnosis of malaria. Clin. Microbiol. Infect. 9: 497-504.
10. Moody, A. 2002. Rapid diagnostic test for malaria parasites. Clin. Microbiol. Rev. 15: 66-78.
11. Murray, C. K., D. Bell, R. A. Gasser, and C. Wongsrichanalai. 2003. Rapid diagnostic testing for malaria. Trop. Med. Int. Health. 8: 876-883.
12. Rubio, J. M., I. Buhigas, M. Subirats, M. Baquero, s. Puento, and A. Benito. 2001. Limited level of accuracy provided by available rapid diagnosis tests for malaria enhances the need for PCR-based reference laboratories. J. Clin. Microbiol. 39:2736-2737.
13. Craig, M. H., B. L. Bredenkamp, C. H. Williams, E. L. Rossouw, V. J. Kelly, l. Kleinschmidt, A. Martineau, and G. F. Henry. 2002. Field and laboratory comparative evaluation of ten rapid malaria tests. Trans. R. Soc. Med. Hyg. 96: 258-265.
14. Brown, A. E., K. C. Kain, J. Pipithkul, and H. K. Webster. 1992. Demonstration by the polymerase chain reaction of mixed *Plasmodium falciparum* and *P. vivax* infections undetected by conventional microscopy. Trans. R. Soc. Trop. Med. Hyg. 86: 609-612.
15. Morassin, B., R. Fabre, A. Berry, and J. F. Magnaval. 2002. One year's experience with the polymerase chain reaction as routine method for the diagnosis of imported malaria. Am. J. Trop. Med. Hyg. 66: 503-508.
16. Patsoula, E., G. Spanakos, D. Sofianatou, M. Parara, and N. C. Vakalis. 2003. A single-step, PCR-based method for the detection and differentiation of *Plasmodium vivax* and *P. falciparum*. Am. Trop. Med. Parasitol. 97: 15-21.
17. Lee, M. A., C. H. Tan, L. T. Aw, C. S. Tang, M. Singh, S. H. Lee, H. P. Chia, and E. P. H. Yap. 2002. Real-time fluorescence-based PCR for detection of malaria parasites. J. Clin. Microbiol. 40: 4343-4345.
18. Perandin, F., N. Manca, A. Calderaro, G. piccolo, L. Galati, L. Ricci, M. C. Medici, M. C. Arcangeletti, G. Snounou, G. Dettori, and C. Chezzi. 2004. Development of a real-time PCR assay for detection of *Plasmodium falci-*

*parum, Plasmodium vivax*, and *Plasmodium oval* for routine clinical diagnosis. J. Clin. Microbiol. 42: 1214-1219.

19. Mangold K. A., R. U. Manson, E. S. C. Koay, L. Stephens, M. Regner, R. B. Thomson, L. R. Peterson, and K. L. Kaul. 2005. Real-time PCR for detection and identification of Plasmodium spp. J. Clin. Microbiol. 43: 2435-2440.

20. Pierce, P. F, W. K. Milihous, and C. C. Campbell. 1987. Clinical and laboratory characterization of a chloroquine-resistant *Plasmodium falciparum* strain acquired in the Central African Republic. Am. J. Trop. Med. Hyg. 36: 1-2.

21. Belec, L., J. Delmont, l. Vesters, T. Testa, K. S. Christian, and A. J. Georges. 1988. Emergence of multiresistant *Plasmodium falciparum* malaria in Central African Republic. Press Med. 17: 2090-2091.

22. Menard, D., N. Madji, A. Manirakiza, D. Djalle, M. R. Koula, and A. Talarmin. 2005. Efficacy of chloroquine, amodiaquine, sulfadoxine-pyrimethamine, chloroquine-sulfadoxine-pyrimethamine combination, and amodiaquine-sulfadoxine-pyrimethamine combination in Central African children with noncomplicated malaria. Am. J. Trop. Med. Hyg. 72: 581-585.

23. Marquino, W., L. Ylquimiche, Y. Hermenegildo, A. M. Palacios, E. Falconi, C. Cabezas, N. Arrospide, S. Gutierrez, and T. K. Ruebush. 2005. Efficacy and tolerability of artesunate plus sulfadoxine-pyrimethamine and sulfadoxine-pyrimethamine alone for the treatment of uncomplicated *Plasmodium falciparum* malaria in Peru. Am. J. Trop. Med. Hyg. 72: 568-572.

24. Bloland, P. B., P. N. Kazembe, A. J. Oloo, B. Himonga, I. M. Barat, and T. K. Ruebush. 1998. Chloroquine in Africa: critical assessment and recommendations for monitoring, and evaluating chloroquine therapy efficacy in sub-Saharan Africa. Trop. Med. Int. Health 3: 543-552.

25. White, N. J. 1999. Delaying antimalarial drug resistance with combination chemotherapy. Parassitologia 41: 301-308.

26. Oaks, S. C. J. R., V. S. Mitchell, G. W. Pearson, and C. C. J. Carpenter. 1991. Malaria: Obstacles and Opportunities. Washington DC: National Academy Press.

27. Cox, F. E. G. 1992. Malaria Vaccine-Progress and Problems. Tibtech 9: 389-394.

28. Nussenzweig, V., and R. S. Nussenweig. 1986. Development of a sporozoite malaria vaccine. Am. J. Trop. Med. Hyg. 35: 678-688.

29. Khusmith, S., Y. Charoenvit, S. Kumar, M. Sedegah, R. L. Beaudoin, and S. L. Hoffman. 1991. Protection against malaria by vaccination with sporozoite surface protein 2 plus CS protein. Science 252: 715-718.

30. Szarfman, A., J. A. Lyon, D. Walliker, et al. 1988. Mature liver stages of cloned *Plasmodium falciparum* share epitopes with proteins from sporozoites and a sexual blood stages. Parasite Immunol. 10: 339-351.

31. Zhu, J., and M. R. Hollingdale. 1991. Structure of *Plasmodium falciparum* liver stage antigen-1. Mol. Biochem. Parasitol. 48: 223-226.

32. Holder, A. A. 1988. The precursor to major merozoite surface antigen: Structure and role in immunity. Prog. Allergy 41: 72.

33. Thomas, A. W., D. A. Carr, J. M. Carter, and J. A. Lyon. 1990. Sequence comparison of allelic forms of the *Plasmodium falciparum* merozoite surface antigen MSA2. Mol. Biochem. Parasitol. 43: 211-220.

34. Lee Sim, B. K., P. A. Orlandi, J. D. Haynes, et al. 1990. Primary structure of the 175K *Plasmodium falciparum* erythrocyte binding antigen and identification of a peptide which elicits antibodies that inhibit malaria merozoite invasion. J. Cell. Biol. 111: 1877-1884.

35. Inselburg, J., D. J. Bzik, W. B. Li, et al. 1991. Protective immunity induced in Aotus monkeys by recombinant SERA proteins of *Plasmodium falciparum*. Infect. Immun. 59: 1247-1250.

36. Nolte, D., E. Hundt, G. Langsley, and B. Knapp. 1991. A *Plasmodium falciparum* blood stage antigen highly homologous to the glycophorin binding protein GBP. Mol. Biochem. Parasitol. 49: 243-264.

37. Rener, J., P. M. Graves, R. Carter, J. L. Williams, and T. R. Burkot. 1983. Target antigens of transmission-bloking immunity on gametes of *Plasmodium falciparum*. J. Exp. Med. 158: 976-981.

38. Vermeulen, A. N., T. Ponnudurai, P. J. A. Beckers, J. Verhave, M. A. Smits, and J. H. E. Meuwissen. 1985. Sequential expression of antigens on sexual stages of *Plasmodium faciparum* accessible to transmission-blocking antibodies in the mosquito. J. Exp. Med. 162:1460-1476.

39. Rungruang, T., O. Kaneko, Y. Murakami, T. Tsuboi, T. Kinoshita, and M. Torii. 2004. A glycosylphosphatidyl inositol anchored protein is a critical erythrocyte surface receptor for the malaria parasite. Molecular Parasitology Meeting XV. Sep. 19-23, 2004. Marine Biological Laboratory, Woods Hole, Mass. (USA).

40. Freeman, R. R., and A. A. Holder. 1983. Surface antigens of malaria merozoites. A high molecular weight precursor is processed to an 83,000 mol wt form expressed on the surface of *Plasmodium falciparum* merozoites. J. Exp. Med. 158: 1647-1653.

41. Hall, R., A. Osland, J. E. Hyde, D. L. Simmons, I. A. Hope, and J. G. Scaife. 1984. Processing, polymorphism, and biological significance of p190, a major surface antigen of the erythrocytic forms of *Plasmodium falciparum* . Mol. Biochem. Parasitol. 11: 61-80.

42. Chang, S. P., G. S. N. Hui, A. Kato, and W. A. Siddiqui. 1989. Generalized immunological recognition of the major merozoite surface antigen (gp195) of *Plasmodium falciparum*. Proc. NatI. Acad. Sci. USA 86: 6343-6367.

43. Blackman, M. J., H. G. Heidricch, S. Donachie, J. S. McBride, and A. A. Holder. 1990. A single fragment of a malaria merozoite surface protein remains on the parasite during red cell invasion and is the target of invasion inhibiting antibodies. J. Exp. Med. 172: 379-382.

44. Trager, W., and J. B. Jensen. 1976. Human malaria parasites in continuous culture. Science 193: 673-675.

45. Sambrook, J., E. F. Fritsch, and T. Maniatis. 1989. Molecular cloning: A laboratory manual, $2^{nd}$ ed. Cold Spring Harbord Laboratory, Cold Spring Harbord, N.Y.

46. Saiki, R. K., S. Scharf, F. Falooma, K. B. Mullis, C. T. Horn, H. A. Erlich, and N. Arnheim. 1985. Amplification of β-globine genomic sequences and restriction site analysis for diagnosis of sickle cell anemia. Science 230: 1350-1354.

47. Kawasaki, E. S., and A. M. Wang. 1989. Detection of gene expression. PCR technology. H. A., Erlich (ed.) New York, Stockton. 89-97.

48. Chang, S. P., K. J. Kramer, K. M. Yamaga, A. Kato, S. E. Case, and W. A. Siddiqui. 1988. *Plasmodium falciparum*: Gene structure and hydropathy profile of the major merozoite surface antigen (gp195) of the Uganda-Palo Alto isolate. Exp. Parasitol. 67: 1-11.

49. Southern, E. M. 1975. Detection of specific sequences among DNA fragments separated by gel electrophoresis. Mol. Biol. 98: 503-517.

50. Sambrook, J., E. F. Fritsch, and T. Maniatis. 1989. Extraction, purification and analysis of messenger RNA from eukariotic cells. In Molecular Cloning, a Laboratory Manual, $2^{nd}$ Ed., Cold Spring Harbor: N.Y., Cold Spring Harbor Laboratory Press, 7.28-7.52.

51. Nguyen, K. V. 2005. Utilization of nucleotide probes in ELISA procedure for the quantitative determination of baculovirus titer. Anal. Lett. (submitted).

52. Howard, R. J., J. A. Lyon, C. L., Diggs, J. D. Haynes, J. H. Leech, J. W. Barnwell, S. B. Aley, M. Aikawa, and L. H. Miller. 1984. Localization of the major *Plasmodium falciparum* glycorotein on the surface of mature intraerythrocytic trophozoites and schizonts. Mol. Biochem. Parasitol. 11: 349-362.

53. Etlinger, H. M., P. Caspers, H. Matile, H. J. Schoenfeld, D. Stueber, and B. Takacs. 1991. Ability of recombinant or native proteins to protect monkeys against heterologous challenge with *Plasmodium falciparum*. Infect. Immun. 59: 3498-3503.

54. Hall, R., J. E. Hyde, M. Goman, D. L. Simmons, I. A. Hope, M. Mackay, J. Scaife, B. Merkli, R. Richle, and J. Stocker. 1984. Major surface antigen gene of human malaria parasite cloned and expressed in bacteria. Nature (London) 311: 379-382.

55. Siddiqui, W. A., L. Q. Tam, K. J. Kramer, G. S. N. Hui, S. E. Case, K. M. Yamaga, S. P. Chang, E. B. T. Chan, and S. C. Kan. 1987. Merozoite surface coat precyrsor protein completely protects Aotus monkeys against *Plasmodium falciparum* malaria. Proc. Aatl. Acad. Sci. USA 84: 3014-3018.

56. Daly, T. M., and C. A. Long. 1993. A recombinant 15-kilodalton carboxylterminal fragment of Plasmodium yoelii yoelii 17XL merozoite surface protein-1 induces a protective response in mice. Infect. Immun. 61: 2462-2467.

57. Ling, I. T., S. A. Ogun, and A. A. Holder. 1994. Immunization against malaria with a recombinant protein. Parasite Immunol. 16: 63-67.

58. Chang, S. P., H. L. Gibson, C. T. Lee-Ng, P. J. Barr, and G. S. N. Hui. 1992. A carboxyl-terminal fragment of *Plasmodium falciparum* gp195 expressed by a recombinant baculovirus induces antibodies that completely inhibit parasite growth. J. Immunol. 149: 548-555.

59. Chang, S. P., S. E. Case, W. L. Gosnell, A. Hashimoto, K. J. Kramer, L. Q. Tam, C. Q. Hashiro, C. M. Nikaido, H. L. Gibson, C. T. Lee-ng, P. J. Barr, B. T. Yokota, and G. S. N. Hui. 1996. A recombinant baculovirus 42-Kda C-terminal fragment of *Plasmodium falciparum* merozoite surface protein 1 protects Aotus monkeys against malaria. Infect. Immun. 64: 253-261.

TABLE 1

Efficiency of the biotin label probes 7, 8, and 9 for the detection of the 42-kDa C-terminal region of the MSP1 gene determined by ELISA [a], [b], [c] ($O.D._{\lambda=405\ nm}$).

| Biotin label | Absence of digoxigenin-11-dUTP Lanes No. | | | Presence of digoxigenin-11-dUTP Lanes No. | | |
|---|---|---|---|---|---|---|
| Probes No. | 1 | 2 | 3 | 4 | 5 | 6 |
| 7 | 0.131 | 0.127 | 0.133 | 0.209 | 1.584 | 1.328 |
| 8 | 0.123 | 0.128 | 0.140 | 0.163 | 1.695 | 1.421 |
| 9 | 0.117 | 0.124 | 0.147 | 0.132 | 0.737 | 0.721 |

[a] The $O.D._{\lambda=405\ nm}$ values of the substrate solution for alkaline phosphatase are 0.127, 0.138, and 0.126.
[b] Lanes 1 and 4: Negative control (absence of *P. falciparum* DNA)
[c] Lanes 2, 3, 5, and 6: Positive samples (presence of *P. falciparum* DNA)

TABLE 2

Quantitative determination of the 42-kDa C-terminal region of the MSP1 gene by ELISA [a], [b] ($O.D._{\lambda=405\ nm}$).

| Biotin label | Presence of digoxigenin-11-dUTP Lanes No. | | | | | |
|---|---|---|---|---|---|---|
| Probes No. | 1 | 2 | 3 | 4 | 5 | 6 |
| 8 (0.56 ng) | 0.920 | 0.860 | 0.968 | 0.588 | 0.538 | 0.474 |
| 8 (1.4 ng) | 1.960 | 1.814 | 1.993 | 1.114 | 0.925 | 0.839 |
| 7 + 8 + 9 (0.56 ng each) | 2.511 | 1.991 | 2.178 | 1.296 | 0.878 | 0.830 |

[a] The $O.D._{\lambda=405\ nm}$ values are the mean of duplicate.
[b] Lanes 1 to 6: The concentration of the *P. falciparum* DNA (μg/mL): 550, 275, 137.50, 68.75, 34.375, and 17.185 μg/mL for the lanes 1 to 6 respectively.

What is claimed is:

1. A procedure using specific biotin labeled nucleotide probes directed to the highly conserved 42-kDa C-terminal region of the *Plasmodium falciparum* merozoite surface protein 1 (MSP1) gene as a target for the quantitative determination of *Plasmodium falciparum* DNA, comprising:

(a) a procedure for amplifying the 42-kDa C-terminal region of the MSP1 gene from negative control (non-infected) and *P. falciparum* infected samples by polymerase chain reaction (PCR) comprising the following steps:

(i) isolating *P. falciparum* DNA from the negative control and *P. falciparum* infected samples; and (ii) PCR amplifying the DNA of step (a)(i) in the presence of digoxigenin-11-dUTP using the oligonucleotides SEQ ID NO: 1 and SEQ ID NO: 2 under the following PCR conditions: denaturing at 94° C. for 1 minute; annealing at 55° C. for 2 minutes; elongating at 72° C. for 1 minute each cycle, for 20 cycles; thereby producing PCR products in which the 42-kDa C-terminal region of the MSP1 gene amplified from said samples is conjugated to digoxigenin-11-dUTP;

(b) a procedure for the synthesis of three specific biotin labeled nucleotide probes 7, 8, and 9 directed respectively to three different fragments of 420 bp (fragment 1), 420 bp (fragment 2), and 379 bp (fragment 3) located in the 42-kDa C-terminal region of the MSP1 gene of *P. falciparum* comprising the following steps:

(i) performing a PCR reaction using the 42-kDa C-terminal region of the *P. falciparum* MSP1 gene as template and the oligonucleotides SEQ ID NO: 1, SEQ ID NO: 2, SEQ ID NO: 3, SEQ ID NO: 4, SEQ ID NO: 5, and SEQ ID NO: 6 as primers, under the following PCR conditions: denaturing at 94° C. for 1 minute; annealing at 65° C. for 2 minutes; elongating at 72° C. for 1 minute each cycle, for 35 cycles; wherein SEQ ID NO: 1 and SEQ ID NO: 3 amplify fragment 1, SEQ ID NO: 4 and SEQ ID NO: 5 amplify fragment 2, and SEQ ID NO: 2 and SEQ ID NO: 6 amplify fragment 3;

(ii) ligating amplified fragments 1, 2, and 3 produced in step (b)(i) into the pCR$^R$2.1 plasmid vector and introducing ligation products into *E. coil* strain TOP10F', thereby producing vectors 4, 5, and 6 comprising fragments 1, 2, and 3, respectively;

(iii) isolating SpeI-XhoI fragments containing fragments 1, 2, and 3 from vectors 4, 5, and 6 respectively; and (iv) synthesizing three specific biotin labeled nucleotide probes 7, 8, and 9 using the SpeI-XhoI fragment isolated from vector 4 as template and SEQ ID NO: 1 and SEQ ID NO: 3 as primers to synthesize probe 7, the SpeI-XhoI fragment isolated from vector 5 as template and SEQ ID NO: 4 and SEQ ID NO: 5 as primers to synthesize probe 8, and the SpeI-XhoI fragment isolated from vector 6 as template and SEQ ID NO: 2 and SEQ ID NO: 6 as primers to synthesize probe 9; and (c) using the PCR products produced in (a) and probes 7, 8, and 9 synthesized in (b) in an enzyme linked immunosorbent assay (ELISA) to quantitatively determine the 42-kDa C-terminal region of the MSP1 gene in said samples, and thereby quantitatively determining *P. falciparum* DNA in said samples.

* * * * *

SEQUENCE LISTING

<160> NUMBER OF SEQ ID NOS: 6

<210> SEQ ID NO 1
<211> LENGTH: 50
<212> TYPE: DNA
<213> ORGANISM: unknown
<220> FEATURE:
<223> OTHER INFORMATION: protozoa

<400> SEQUENCE: 1
attggatcca ctaaaatgtg gtcttggaag tgtcttttat tctgggctgt    50

<210> SEQ ID NO 2
<211> LENGTH: 37
<212> TYPE: DNA
<213> ORGANISM: unknown
<220> FEATURE:
<223> OTHER INFORMATION: protozoa

<400> SEQUENCE: 2
cgtaggtacc ttattaaggt ggggagcaga agatacc    37

```
<210> SEQ ID NO 3
<211> LENGTH: 21
<212> TYPE: DNA
<213> ORGANISM: unknown
<220> FEATURE:
<223> OTHER INFORMATION: protozoa

<400> SEQUENCE: 3
gaacttgatg tcgttctcaa c                                          21

<210> SEQ ID NO 4
<211> LENGTH: 21
<212> TYPE: DNA
<213> ORGANISM: unknown
<220> FEATURE:
<223> OTHER INFORMATION: protozoa

<400> SEQUENCE: 4
gttgagaacg acatcaagtt c                                          21

<210> SEQ ID NO 5
<211> LENGTH: 22
<212> TYPE: DNA
<213> ORGANISM: unknown
<220> FEATURE:
<223> OTHER INFORMATION: protozoa

<400> SEQUENCE: 5
cagttttcca agcatgtctt tc                                         22

<210> SEQ ID NO 6
<211> LENGTH: 22
<212> TYPE: DNA
<213> ORGANISM: unknown
<220> FEATURE:
<223> OTHER INFORMATION: protozoa

<400> SEQUENCE: 6
gaaagacatg cttggaaaac tg                                         22
```